United States Patent
Pinkos

(10) Patent No.: US 8,236,996 B2
(45) Date of Patent: Aug. 7, 2012

(54) PROCESS FOR PREPARING 1,6-HEXANEDIOL

(75) Inventor: Rolf Pinkos, Bad Duerkheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/303,857

(22) Filed: Nov. 23, 2011

(65) Prior Publication Data

US 2012/0071624 A1    Mar. 22, 2012

Related U.S. Application Data

(63) Continuation of application No. 12/952,956, filed on Nov. 23, 2010, now Pat. No. 8,124,815.

(30) Foreign Application Priority Data

Nov. 26, 2009  (DE) .......................... 10 2009 047 196

(51) Int. Cl.
*C07C 31/20* (2006.01)

(52) U.S. Cl. ...................................... 568/852; 568/868

(58) Field of Classification Search .................. 568/852, 568/868
See application file for complete search history.

(56) References Cited

U.S. PATENT DOCUMENTS

| | | |
|---|---|---|
| 6,426,438 B1 | 7/2002 | Fischer et al. |
| 2010/0191018 A1 | 7/2010 | Teles et al. |
| 2010/0256398 A1 | 10/2010 | Pinkos et al. |

FOREIGN PATENT DOCUMENTS

| | | |
|---|---|---|
| DE | 101 12 117 A1 | 9/2002 |
| WO | 97/31882 A1 | 9/1997 |
| WO | WO 2009/080504 A1 | 7/2009 |
| WO | WO 2010/086314 A1 | 8/2010 |
| WO | WO 2010/115759 A2 | 10/2010 |

OTHER PUBLICATIONS

International Search Report issued in PCT/EP2010/067881 dated Feb. 28, 2011.

*Primary Examiner* — Elvis O Price

(74) *Attorney, Agent, or Firm* — Oblon, Spivak, McClelland, Maier & Neustadt, L.L.P.

(57) ABSTRACT

The invention provides 1,6-hexanediol having a proportion by weight of nitrogen of less than 5 ppm, and polymers obtained by reacting the 1,6-hexanediol with at least one reactive compound. The 1,6-hexanediol is obtained by distilling a mixture including 1,6-hexanediol and more than 500 ppm of at least one carboxylic acid, ester, or both, having a boiling point higher than that of the 1,6-hexanediol and being in contact with the 1,6-hexanediol at a temperature range greater than or equal to 100° C. for at least 5 minutes before, during, or before and during, the distillation, followed by collection of the 1,6-hexanediol. In certain embodiments of this invention, the 1,6-hexanediol has a proportion by weight of nitrogen of less than 3 ppm and less than 2 ppm.

20 Claims, No Drawings

PROCESS FOR PREPARING 1,6-HEXANEDIOL

CROSS-REFERENCE TO RELATED APPLICATIONS

This application is a continuation of U.S. patent application Ser. No. 12/952,956 filed Nov. 23, 2010 and claims priority of German patent application No. 10 2009 047 196.0 filed Nov. 26, 2009.

BACKGROUND OF THE INVENTION

The invention relates to a process for preparing 1,6-hexanediol, in which a hexanediol having a proportion by weight of nitrogen of less than 5 ppm is obtained, 1,6-hexane-diol having a proportion by weight of nitrogen of less than 5 ppm and also the use of this 1,6-hexanediol for preparing polymers.

There is a great demand for 1,6-hexanediol which has no amines in amounts which have a catalytic effect in the preparation of polyurethanes, since these catalytic amounts of amines lead to considerable amounts of by-products which hinder the reaction to form the polyurethane.

DE 10112117 A1 describes a process for removing nitrogen-comprising compounds using acidic and/or basic ion exchangers. The proportion by weight of nitrogen is determined here by means of a CPR (controlled polymerization rate). This purification process has the disadvantage that the use of acidic and/or basic ion exchangers leads to increased costs since the ion exchangers themselves represent costs and their use means an increased use of solvents since ion exchangers are only finitely useable and have to be regenerated every now and again. In addition, to avoid losses of product, rinsing of the ion exchanger is necessary and leads to increased use of solvents or regeneration media. Since 1,6-hexanediol is solid under normal conditions, the feed to the ion exchanger has to be additionally heated for a reaction over the ion exchanger to be possible at all. Thus, the process for purifying polyalcohols in DE 101112117 A1 has considerable disadvantages. Furthermore, DE 101112117 A1 does not describe the removal of nitrogen-comprising compounds from 1,6-hexanediol.

The preparation of 1,6-hexanediol starts out from the appropriate cyclo-$C_6$-alkanes, alcohols, ketones and/or mixtures of these compounds, and these are either oxidized in the presence of nitric acid and/or subjected to oxidation with subsequent water extraction of the organic stream.

In the case of 1,6-hexanediol, streams comprising adipic acid are produced in this way from, for example, cyclohexanol and/or cyclohexanone by oxidation using nitric acid. For the present purposes, streams comprising adipic acid are streams which can comprise adipic acid itself or else adipic acid in the form of its esters. In the oxidation, it is possible to use both the adipic acid obtained by oxidation and the mixture remaining after the adipic acid has largely been separated off, which mixture comprises adipic acid, glutaric acid and succinic acid.

Furthermore, other sources of adipic acid or streams comprising adipic acid are in principle streams which can be mixed with the abovementioned streams, for example streams obtained by oxidation of cyclohexane to cyclohexanol/cyclohexanone mixtures and subsequent water extraction of the organic stream.

The abovementioned streams usually comprise impurities which in the case of the oxidation of cyclohexanol/cyclohexanone are formed by oxidation using nitric acid and comprise nitrogen. Nitrogen components are also present as undesirable secondary components in the water extracts after the oxidation of cyclohexane by means of air.

These nitrogen compounds, which can be present, for example, as nitro group, amides or ammonium ion, are able to form amines during the hydrogenation of streams comprising adipic acid, which can also be esterified. For example, nitro compounds can be hydrogenated directly to amines and/or amides. Ammonium ions can aminate alcohols formed during the hydrogenation.

Amines are basic components and as such are undesirable in 1,6-hexanediol since they have properties which are undesirable in the uses of 1,6-hexanediol. Thus, these amines can, for example, have a catalytic action in the preparation of polyurethanes, so that process control for preparing a product having precisely defined properties is difficult if not impossible. It can happen that entire production batches have to be disposed of. This also applies in principle in the preparation of polyesters or polyester alcohols which are then again reacted further with isocyanates to form urethanes.

One possible way of establishing whether undesirable N-comprising compounds are present in the form of basically acting amines in 1,6-hexanediol is to determine the CPR (controlled polymerization rate). The content of basically acting amine is accordingly coupled with the CPR and can, as explained for the example of 1,6-hexanediol, be determined as follows:

> 30 g of 1,6-hexanediol are dissolved in 100 ml of a solution of potassium hydroxide in methanol (0.001 mol/l) and stirred for 15 minutes. This solution is, for example, titrated potentiometrically with 0.01N hydrochloric acid to the end point using a Titroprocessor 682™ from Metrohm, Herison, Switzerland. The Titroprocessor 682 is equipped with two pH electrodes, viz. a glass electrode (3 M KCl, Metrohm 6.0133.100) and an Ag/AgCl/LiCl electrode (alcohol, Metrohm 6.0726.100). The procedure is repeated using a comparative solution comprising 100 ml of a solution of potassium hydroxide in methanol (0.001 mol/l) to determine the blank.

The CPR is determined from the two results of potentiometric titration as follows:

$$CPR = 10 \times (V1 - V2), \text{ where}$$

V1 is the consumption of 0.01N hydrochloric acid in the case of the polyalcohol sample, V2 is the consumption in the comparison (blank) and 10 corresponds to the calculation factor in accordance with JIS (Japan Industrial Standard) K 1557-1970.

For example, at a CPR of 10, i.e. a net hydrochloric acid consumption of 1 g of 0.01 molar HCl, about 5 ppm of N is present in the 1,6-hexanediol. Such a CPR of 10, i.e. an N content of 5 ppm, is already an undesirably high level and can cause considerable secondary reactions in subsequent polyurethane reactions.

It is therefore an object of the present invention to provide a process which makes it possible to prepare 1,6-hexanediol having a CPR of less than 10, without an additional outlay and costs associated with additional solvents and/or acidic and/or basic ion exchangers having to be incurred.

BRIEF SUMMARY OF THE INVENTION

This object is achieved by a process for purifying 1,6-hexanediol, which comprises the following steps I) provision of a mixture comprising 1,6-hexanediol
II) distillation of this mixture from step I
III) collection of a 1,6-hexanediol having a nitrogen content of less than 5 ppm, wherein more than 500 ppm of carboxylic acids and/or esters which have a boiling point higher than that of 1,6-hexanediol and are in contact with the 1,6-hexanediol at temperatures of $\geq 100°$ C. for at least 5 minutes are comprised before and/or during the distillation in step II.

DETAILED DESCRIPTION OF THE INVENTION

In the process of the invention, it is necessary for the mixture from step I of the process of the invention which is to be distilled to comprise not only 1,6-hexanediol but also carboxylic acids and/or esters which have a boiling point higher than that of 1,6-hexanediol itself. This can be achieved by the mixture used in step I) comprising not only 1,6-hexanediol but also carboxylic acids and/or esters which form higher-boiling esters with 1,6-hexanediol or else, before and/or during the distillation in step II, either carboxylic acids and/or esters having a boiling point higher than that of 1,6-hexanediol (high boilers) being added to the mixture from step I or carboxylic acids and/or esters which react with part of the 1,6-hexanediol to form esters which after the reaction have a boiling point higher than that of 1,6-hexanediol are added. It is also possible to use mixtures of high boilers and carboxylic acids and/or esters which with 1,6-hexanediol form esters having a boiling point higher than that of 1,6-hexanediol itself.

When high boilers or carboxylic acids and/or esters which form higher-boiling esters with 1,6-hexanediol itself are added before and/or during the actual distillation in step II, then the distillation has to be carried out so that these high boilers and/or higher-boiling esters are in contact with the 1,6-hexanediol in the mixture from step I for a particular time before the 1,6-hexanediol is distilled off. This contact time during the distillation has to be at a temperature of $\geq 100°$ C. for at least 5 minutes. Preference is given to a contact time of $\geq 10$ minutes, particularly preferably a contact time of $\geq 15$ minutes. For the purposes of the present invention, the contact time is the time for which the 1,6-hexanediol is in contact with the high boiler and/or the higher-boiling esters in the liquid or gaseous state within the column. The contact space in which the 1,6-hexanediol has to be in contact with the high boiler and/or the higher-boiling esters is the entire column and also the associated piping and, if appropriate, the vaporizer. The contact space thus comprises the packing within the column, the collectors and distributors and also the associated piping, the bottom of the column and also any attached vaporizer and the pipe to this.

The temperature during the contact time should be $\geq 100°$ C., preferably at least 120° C., particularly preferably at least 140° C.

The carboxylic acids and/or esters which are if appropriate added to the mixture from step I before the distillation in step II are selected from the group consisting of adipic acid, adipic esters, 6-hydroxycaproic acid, 6-hydroxycaproic esters. Particular preference is given to the esters selected from the group consisting of dimethyl adipate, methyl 6-hydroxycaproate, 1,6-hexanediol methyl adipate, the di-1,6-hexanediol ester of adipic acid, the 1,6-hexanediol ester of 6-hydroxycaproic acid and mixtures of these esters.

The amount of carboxylic acids and/or esters which are reacted with the 1,6-hexanediol to form the higher-boiling esters and also the amount of high boilers added and the amount of mixtures of added high boilers and carboxylic acids and/or esters which are reacted with 1,6-hexanediol to form the higher-boiling esters are in the range of $\geq 500$ ppm, preferably in the range of $\geq 1000$ ppm, particularly preferably $\geq 1500$ ppm, based on the amount of 1,6-hexanediol to be distilled.

The pressures during the distillation are preferably in the range from 5 to 3000 mbar absolute. Before the actual distillation in step II of the process of the invention, other compounds can, if appropriate, be distilled off beforehand. These are in particular compounds which have a boiling point at least 50° C. lower than that of 1,6-hexanediol itself and are referred to as low boilers. The low boilers are preferably selected from the group consisting of methanol, water, dimethyl ether, 1-hexanol and 1-methoxy-6-hydroxyhexane. The low boilers can be separated off in a separate column which is located upstream of the distillation in step II. The pressure within this column for separating off the low boilers is, for example when methanol and/or water are to be separated off, in the range from 200 to 3000 mbar absolute, and when 1,6-hexanediol is to be separated off from high boilers and/or the higher-boiling esters, the pressure during this distillation is in the range from 5, preferably 10 to 500 mbar absolute, preferably in the range from 20 to 300 mbar absolute, particularly preferably in the range from 30 to 200 mbar absolute.

The distillations can be carried out as batch process or continuously, but preference is given to continuous operation, especially when 1,6-hexanediol is to be produced in industrial amounts.

To prepare 1,6-hexanediol having a proportion by weight of nitrogen of less than 5 ppm, adipic acid which has been prepared either by oxidation of cyclohexanol and/or cyclohexanone by means of nitric acid, by oxidation of cyclohexane to cyclo-hexanol/cyclohexanone mixtures and subsequent water extraction of the organic stream or by oxidation of cyclohexane by means of air and subsequent water extraction is used as starting material. Here, the adipic acid comprising the solutions is esterified with an alcohol selected from the group consisting of methanol, ethanol, propanol, isopropanol, n-butanol, isobutanol, pentanols, hexanols, 2-ethylhexanol, 2-propylheptanol, 1,5-pentanediol, 1,6-hexanediol, tridecanol, pentadecanol and mixtures of the alcohols, preferably methanol, ethanol, propanol, n-butanol and 1,6-hexanediol. Particular preference is given to methanol and 1,6-hexanediol for esterification. The subsequent hydrogenation can be carried out in the gas phase or in the liquid phase.

When the subsequent hydrogenation is to be carried out in the gas phase, methanol is preferred as alcohol for esterification.

If hydrogenation is to be carried out in the liquid phase, not only methanol but also 1,6-hexanediol are preferred.

The alcohol is used in an at least equimolar amount relative to the carboxyl groups of the adipic acid and, if appropriate, other carboxyl groups of other acids which may be present. However, preference is given to a molar excess of alcohol per carboxyl group of at least 2.

The esterification can proceed without added catalyst, but preference is given to using one catalyst after an acid conversion of 50% by weight. This can be, for example, sulfuric acid or sulfonic acids, but also acidic solids such as ion exchangers, usually ion exchangers based on sulfonic acid.

The water of reaction formed is preferably separated off during the esterification, e.g. by distillation. Alcohol is also entrained. For this reason, preference is given to distilling the alcohol/water mixture separately and recirculating the alcohol.

Depending on the esterification technology, the dialkyl adipate can be obtained in a form ready for use in the hydrogenation, but it can also be that alcohol and water still have to be separated off or the dialkyl adipate has to be purified by distillation in order to separate off incompletely reacted acid which is either disposed of or preferably, if appropriate after discharge of a small percentage to avoid accumulation of undesirable components, recirculated to the esterification. The optionally purified dialkyl adipate is subsequently hydrogenated.

This can occur in the liquid phase or gas phase, preferably over Cu-comprising catalysts.

In the liquid-phase hydrogenation, preference is given to employing pressures of 100-330 bar absolute, preferably a gauge pressure of 150-270 bar, while in the gas phase a gauge pressure of from 5 to 100 bar is appropriate, with particular preference being given to from 20 to 70 bar.

It is advantageous for the hydrogenation product mixture still to comprise carboxyl groups, preferably esters. These can be, for example, dimethyl adipate, methyl 6-hydroxycaproate, 1,6-hexanediol methyl adipate, the di-1,6-hexanediol ester of adipic acid and/or the 1,6-hexanediol ester of 6-hydroxycaproic acid. If exclusively or virtually exclusively dimethyl adipate and/or methyl 6-hydroxycaproate are to be present as carboxyl-comprising compounds in the hydrogenation product mixture, it has to be ensured in the subsequent distillation stage(s) or in a separate stage that these esters are not distilled off completely from 1,6-hexanediol. In the process of the invention, these esters are reacted with 1,6-hexanediol at temperatures of $\geq 100°$ C. to form corresponding esters having a boiling point higher than 1,6-hexanediol itself. These corresponding higher-boiling esters are selected from the group consisting of 1,6-hexanediol methyl adipate, the di-1,6-hexanediol ester of adipic acid and/or the 1,6-hexanediol ester of 6-hydroxycaproic acid. The content of these higher-boiling esters based on the content of 1,6-hexanediol is at least 500 ppm, preferably $\geq 1000$ ppm, particularly preferably $\geq 1500$ ppm.

The reaction of dimethyl adipate and methyl 6-hydroxycaproate with 1,6-hexanediol can occur either purely thermally or in the presence of catalytically active compounds such as acids or bases. Preference is given to the thermal variant in which the temperature is $\geq 100°$ C. and the time for which the esters and 1,6-hexanediol are in contact has to be at least 5 minutes. Preference is given to temperatures of $\geq 120°$ C. and contact times of $\geq 10$ minutes.

In a preferred embodiment, if methyl esters have been used in the hydrogenation, at least 50% of the methanol has been removed by distillation before this contact time. This is preferably combined with the methanol removal step which precedes the actual distillation in step II.

The mixture comprising 1,6-hexanediol, the high boilers, higher-boiling esters and if appropriate low boilers is fractionally distilled. Here, compounds having a boiling point lower than that of 1,6-hexanediol, for example the low boilers such as methanol, are preferably separated off by distillation in a first distillation unit, e.g. a continuously operated column. By-products such as water and dimethyl ether are obtained together with the methanol. In the distillation, the energy is preferably introduced via the bottom of the column, for example by means of a bottom circuit. The temperature at the bottom should be at least 100° C. It is advantageous to keep the temperature of the feed to the column above 20° C., for example at the level at which the hydrogenation product mixtures are obtained so that their thermal energy can be utilized in the column. The average residence time of the 1,6-hexanediol together with the abovementioned high boilers and higher-boiling esters at temperatures of at least 100° C. in this column is at least 5 minutes. This 1,6-hexanediol-comprising stream is advantageously processed in a further column to give 1,6-hexanediol having a proportion by weight of nitrogen of less than 5 ppm. Here, it is possible to use, for example, a dividing wall column or a column having a side offtake in which the low boilers such as 1-hexanol, 1-methoxy-6-hydroxyhexane together with very little 1,6-hexanediol are distilled off at the top, high boilers and/or higher-boiling esters which likewise comprise very little 1,6-hexanediol are taken off at the bottom and liquid or gaseous 1,6-hexanediol having a nitrogen content of less than 5 ppm is taken off via the side offtake. This 1,6-hexanediol preferably comprises less than 3 ppm of nitrogen. This column is operated at a temperature at the bottom of above 100° C. and average residence times of more than 5 minutes. The nitrogen-comprising components are discharged to an extent of at least 50% with the high-boiling bottom stream.

Instead of the one column having a side offtake, it is also possible to use two separate columns, with low boilers being removed at the top in the first column and the 1,6-hexanediol then being distilled off from high boilers and/or higher-boiling esters in the second column. A temperature of at least 100° C. with average residence times of at least 5 minutes is set at the bottom of at least the first of the two columns.

To prepare relatively small amounts of 1,6-hexanediol, use can also be made of batch columns in which the hexanediol is purified batchwise. Here, low boilers compared to hexanediol are separated off first, followed by the 1,6-hexanediol itself. High boilers and higher-boiling esters comprising the nitrogen components remain in the bottom.

A further variant is to add carboxyl-comprising components other than carboxylic acids and esters after the hydrogenation. These compounds are, for example, aldehydes and ketones which with the 1,6-hexanediol form compounds which have boiling points higher than that of 1,6-hexanediol itself.

If water is used as solvent, it is useful to hydrogenate the adipic acid itself. As hydrogenation catalyst, it is then possible to use, for example, Co-, Re- and Ru-comprising catalysts. Here too, the conversion of carboxylic acids and/or esters should be incomplete, so that the proportion of carboxylic acids and/or esters in the hydrogenation product mixture is preferably above 500 ppm, particularly preferably above 1000 ppm.

The 1,6-hexanediol prepared in this way, which has a nitrogen (N) content of less than 5 ppm, can be used in any process for preparing polymers in which diols are used. Since the 1,6-hexanediol has an N content of less than 5 ppm, polymers can be obtained therefrom without problems. The 1,6-hexanediol obtained according to the invention is preferably used for the preparation of polyurethanes and polyesters. Here, the 1,6-hexanediol is reacted with diisocyanates such as hexamethylene diisocyanate, tolylene 2,4-diisocyanate, diphenylmethane diisocyanate, isophorone diisocyanate and 4,4'-diisocyanatodicyclohexylmethane to form polyurethanes. To prepare polyesters, the 1,6-hexanediol obtained according to the invention is used in the presence of dicarboxylic acids such as succinic acid, maleic acid, fumaric acid, glutaric acid, adipic acid, dodecanedioic acid, terephthalic acid, isophthalic acid and phthalic acid.

EXAMPLES

Example 1

Adipic acid, obtainable as product of the oxidation of cyclohexanol/cyclohexanone by means of nitric acid, having a content of 4 ppm of nitrogen is esterified by means of an acidic ion exchanger as catalyst (Amberlite IR 120) and methanol to form dimethyl adipate. After complete esterification and removal of the ion exchanger and excess methanol, the ester is distilled (18 mbar, boiling point: 115° C.) and obtained in a purity of 99.98%. The nitrogen (N) content of the ester was 4 ppm. The dimethyl adipate is hydrogenated in the gas phase at 60 bar and 195-210° C. over a copper-comprising catalyst. The space velocity over the catalyst is 0.15 kg of ester feed/liter of catalyst per hour. The reactor is a shaft reactor preceded by a vaporizer in which the feed stream is vaporized at about 195° C. with the aid of a stream of hydrogen gas. The stream of hydrogen gas is composed of fresh gas (4.5 mol/mol of dimethyl adipate) and a recycle gas stream (about 80 mol of hydrogen/mol of feed stream). Downstream of the reactor, the gaseous mixture is cooled and liquid products are taken off. The gaseous output is recirculated by means of a recycle gas compressor. A small part of the gas stream is discharged as offgas. The dimethyl adipate conversion is about 99.9%. A little methanol was lost via the offgas stream. The collected outputs (about 30% by weight of methanol, about 68% by weight of 1,6-hexanediol, about 0.5% by weight of methyl 6-hydroxycaproate and 0.06% by weight of hexanediol ester of 6-hydroxycaproic acid, about 0.3% by weight of hexanol, 0.1% by weight of dimethyl adipate, balance in each case below 0.1% by weight) have an N content of 5 ppm and are worked up by distillation. Here, predominantly methanol is removed at temperatures at the bottom of up to 140° C. and pressures of from 1013 mbar absolute to 100 mbar over a period of one hour. The remaining bottoms (about 0.08% by weight of 1,6-hexanediol methyl adipate, 0.02% by weight of the di-1,6-hexanediol ester of adipic acid, 0.3% by weight of the 1,6-hexanediol ester of 6-hydroxycaproic acid) is fractionally distilled batchwise in a distillation column (1 m packed column, reflux ratio 5, no entry of air) at 100 mbar absolute and temperatures at the bottom of about 185° C. over a period of two hours. After removal of low boilers such as residual methanol and hexanol, 1,6-hexanediol is obtained in a distillation yield of about 90% with a purity of 99.9% and an N content of 1 ppm. The N content in the remaining bottom is 15 ppm.

Comparative Example 1

Example 1 is repeated with the difference that a second reactor which corresponds in terms of dimensions and capacity to the first and through which the reaction mixture flows after the first reactor is additionally installed in the hydrogenation. Accordingly, the space velocity over the catalyst decreases to 0.75. The conversion of dimethyl adipate was virtually quantitative, and the output comprised methanol and hexanediol together with 6-hydroxycaproic esters in the form of methyl and hexanediol esters in amounts of less than 0.03% by weight, about 0.6% by weight of hexanol, a balance in each case less than 0.05% by weight. The output again has an N content of 5 ppm. It is worked up further to give 1,6-hexanediol as in example 1. The resulting 1,6-hexanediol had an N content of 5 ppm, and the bottom product had an N content of 7 ppm.

The invention claimed is:

1. A 1,6-hexanediol having a proportion by weight of nitrogen of less than 5 ppm and obtained by a process comprising:
   I) distillation of a mixture comprising 1,6-hexanediol and more than 500 ppm of at least one carboxylic acid, ester, or both, having a boiling point higher than that of the 1,6-hexanediol and being in contact with the 1,6-hexanediol at a temperature range greater than or equal to 100° C. for at least 5 minutes before, during, or before and during, the distillation; and
   II) collection of the 1,6-hexanediol having a nitrogen content of less than 5 ppm.

2. The 1,6-hexanediol of claim 1, wherein the distillation is carried out in the absence of oxygen.

3. The 1,6-hexanediol of claim 1, wherein the at least one carboxylic acid, ester, or both, is added to the mixture before the distillation.

4. The 1,6-hexanediol of claim 3, wherein the distillation is carried out in the absence of oxygen.

5. The 1,6-hexanediol of claim 1, wherein the mixture comprises at least one ester.

6. The 1,6-hexanediol of claim 2, wherein the mixture comprises at least one ester.

7. The 1,6-hexanediol of claim 3, wherein the mixture comprises at least one ester.

8. The 1,6-hexanediol of claim 1, wherein the distillation is carried out in a range from 10 to 3000 mbar.

9. The 1,6-hexanediol of claim 1, wherein the distillation is carried out batchwise.

10. The 1,6-hexanediol of claim 1, wherein the distillation is carried out continuously.

11. The 1,6-hexanediol of claim 1, wherein the 1,6-hexanediol has a proportion by weight of nitrogen of less than 3 ppm.

12. The 1,6-hexanediol of claim 1, wherein the 1,6-hexanediol has a proportion by weight of nitrogen of less than 2 ppm.

13. The 1,6-hexanediol of claim 1, wherein:
   a) the distillation employs at least one dividing wall;
   b) the distillation employs a column having at least one side offtake, wherein at least one low-boiling compound is distilled off at the top of the column, at least one high-boiling compound is taken off at the bottom of the column, and liquid or gaseous 1,6-hexanediol is taken off at the at least one side offtake; or
   c) the distillation employs at least two separate columns, wherein at least one low-boiling compound is removed at the top of a first column, and the 1,6-hexanediol is distilled off in a second column.

14. A polymer obtained by reacting the 1,6-hexanediol of claim 1 with at least one reactive compound.

15. The polymer of claim 14, wherein the at least one reactive compound comprises a diisocyanate.

16. The polymer of claim 15, wherein the at least one reactive compound comprises at least one selected from the group consisting of hexamethylene diisocyanate, tolylene 2,4-diisocyanate, diphenylmethane diisocyanate, isophorone diisocyanate and 4,4'-diisocyanatodicyclohexylmethane.

17. The polymer of claim 14, wherein the at least one reactive compound comprises a dicarboxylic acid.

18. The polymer of claim 17, wherein the at least one reactive compound is at least one reactive compound comprises at least one selected from the group consisting of succinic acid, maleic acid, fumaric acid, glutaric acid, adipic acid, dodecanedioic acid, terephthalic acid, isophthalic acid and phthalic acid.

19. The polymer of claim 14, wherein the 1,6-hexanediol has a proportion by weight of nitrogen of less than 3 ppm.

20. The polymer of claim 14, wherein the 1,6-hexanediol has a proportion by weight of nitrogen of less than 2 ppm.

* * * * *